United States Patent [19]

Stansbury

[11] Patent Number: 5,145,374

[45] Date of Patent: Sep. 8, 1992

[54] SYNTHETIC DENTAL COMPOSITIONS FORMED FROM CYCLOPOLYMERIZABLE BIS-ACRYLATE AND MULTI-FUNCTIONAL OLIGOMER AND BONDING METHOD

[75] Inventor: Jeffrey W. Stansbury, Gaithersburg, Md.

[73] Assignee: The United States of America as represented by the Secretary of Commerce, Washington, D.C.

[21] Appl. No.: 416,760

[22] Filed: Oct. 3, 1989

[51] Int. Cl.$^5$ ............................................. A61K 5/01
[52] U.S. Cl. ................................. 433/228.1; 433/226
[58] Field of Search .............................. 433/228.1, 226

[56] References Cited

U.S. PATENT DOCUMENTS

| | | |
|---|---|---|
| 3,810,938 | 5/1974 | Schmitt et al. |
| 3,835,090 | 9/1974 | Gander et al. |
| 3,923,740 | 12/1975 | Schmitt et al. |
| 4,041,061 | 8/1977 | Buck |
| 4,041,062 | 8/1977 | Buck |
| 4,041,063 | 8/1977 | Buck |
| 4,067,853 | 2/1978 | Schmitt et al. |
| 4,308,014 | 12/1981 | Kawahara et al. |
| 4,330,283 | 5/1982 | Michl et al. |
| 4,406,625 | 9/1983 | Orlowski et al. |
| 4,433,958 | 2/1984 | Fellmen et al. |
| 4,572,920 | 2/1986 | Rawls et al. |

OTHER PUBLICATIONS

Mathias et al., *Macromolecules*, 1987, 20, pp. 2039–2041; 1988, 21, pp. 545–546.

Primary Examiner—V. Millin
Attorney, Agent, or Firm—Stephen A. Becker; Holly D. Kozlowski

[57] ABSTRACT

Synthetic dental compositions comprise an inorganic filler and a resin formed by polymerization of at least one bis-acrylate of the formula

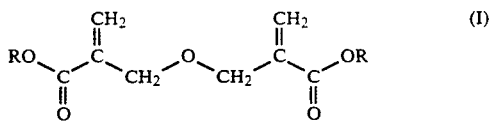

wherein R is selected from the group consisting of alkyl groups having 1 to 6 carbon atoms and aryl substituted alkyl groups in which the alkyl portion has 1 to 6 carbon atoms, or by polymerization of at least one multi-functional oligomer of the formula

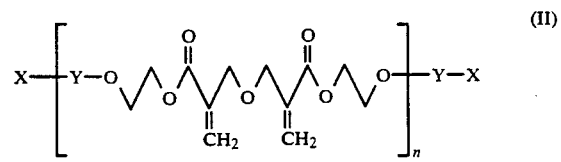

wherein X is the group

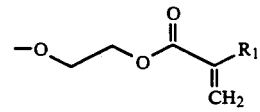

with $R_1$ being H or $CH_2OH$, and Y is a hydrocarbon group having about four to about twenty carbon atoms. Diacids or diacid salts of the hydrolyzed bis-acrylates are also useful in methods for bonding a variety of substrates to teeth.

18 Claims, No Drawings

SYNTHETIC DENTAL COMPOSITIONS FORMED FROM CYCLOPOLYMERIZABLE BIS-ACRYLATE AND MULTI-FUNCTIONAL OLIGOMER AND BONDING METHOD

FIELD OF THE INVENTION

The present invention relates to synthetic dental compositions comprising an inorganic filler and a resin formed by polymerization of at least one bis-acrylate monomer or at least one multifunctional oligomer. The present invention also relates to methods for bonding a variety of substrates to teeth using an adhesive formed from a hydrolyzed diacid of a bis-acrylate monomer.

BACKGROUND OF THE INVENTION

Various synthetic dental compositions comprising resins are known in the art for use in dental fillings, tooth replacement parts, bridges and repair parts. Dental adhesive resins for use in coating or sealing enamel surfaces of teeth to prevent decay and for use in the bonding of brackets and the like to teeth in orthodontics are also known in the art.

For example, the Buck U.S. Pat. Nos. 4,041,061, 4,041,062 and 4,041,063 disclose modified cyanoacrylate monomers which may be homopolymerized or copolymerized to form a highly crosslinked polymer useful in dental adhesive compositions. The Schmitt et al U.S. Pat. Nos. 3,810,938, 3,923,740 and 4,067,853 disclose dental compositions which are formed by polymerization of compounds which are the diesters of acrylic or methacrylic acid with a dihydroxy compound. The Gander et al U.S. Pat. No. 3,835,090 similarly discloses dental compositions comprising a binder formed from trimethacrylate and triacrylate esters of the aliphatic triols glycerol, trimethylolethane, trimethylolpropane and trimethylolbutane.

The Orlowski et al U.S. Pat. No. 4,406,625 discloses compounds which may be polymerized in situ on teeth, which compounds comprise addicts of 1,4-bis[(3-methacroyl-2-hydroxy-propoxy) methyl] cyclohexane and derivatives thereof. The Fellman et al U.S. Pat. No. 4,433,958, the Kawahara et al U.S. Pat. No. 4,308,014, the Michl et al U.S. Pat. No. 4,330,283 and the Rawls et al U.S. Pat. No. 4,572,920 also disclose resins formed from acrylate and/or methacrylate components, which resins are suitable for use in dental compositions.

While these and additional compositions are known for use in dental applications, there is a continuing need for providing synthetic dental compositions which exhibit good durability and adhesion and low shrinkage and which may be easily employed in various dental applications. There is also a continuing need for developing resins for use in dental compositions which may be efficiently polymerized to high degrees of conversion under the conditions imposed by the oral environment.

Mathias et al, *Macromolecules*, 1987, 20, 2039-2041; 1988, 21, 545-546, have disclosed the synthesis and polymerization of a methyl acrylate obtained from reaction of aldehydes and acrylate esters. Mathias et al disclose that the methyl acrylates may be used as cross-linking agents in the polymerization of various vinyl monomers.

SUMMARY OF THE INVENTION

Accordingly, it is an object of the present invention to provide improved synthetic dental compositions which exhibit an advantageous combination of properties. It is a related object of the invention to provide synthetic dental compositions which exhibit good strength, durability and adhesion. It is a further object of the invention to provide compositions which may be easily employed in various dental applications. An additional object of the invention is to provide resins for use in dental compositions, which resins exhibit low shrinkage and are produced with high conversion rates. It is a further object of the invention to provide improved methods for bonding various substrates to teeth.

These and additional objects are provided by the compositions and methods according to the present invention. The synthetic dental compositions of the invention comprise an inorganic filler and a resin formed by polymerization of at least one bis-acrylate of the formula

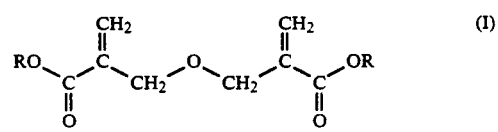

wherein $R_1$ is selected from the group consisting of alkyl groups having 1 to 6 carbon atoms and aryl substituted alkyl groups in which the alkyl portion has 1 to 6 carbon atoms, or by the polymerization of at least one multifunctional oligomer such as that of the formula

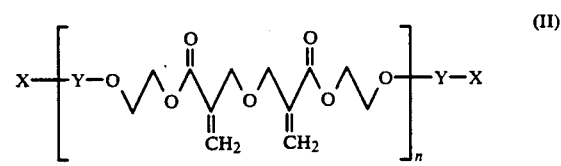

wherein X is the group

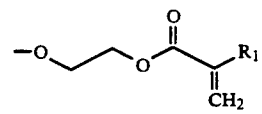

with $R_1$ being H or $CH_2OH$ and Y is a hydrocarbon group having from about four to about twenty carbon atoms. Preferred Y groups include alkylene groups of from about four to about ten carbon atoms and the group

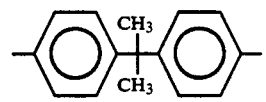

The bis-acrylates and multifunctional oligomers are particularly advantageous for use in the dental compositions of the present invention in that they readily cyclopolymerize. Additionally, the resulting resins exhibit significantly less shrinkage and higher conversion as compared with conventional polymerization products employed in dental compositions. The polymerization products also exhibit good strength properties.

In a further embodiment, the present invention comprises methods for adhesively bonding a substrate to a tooth. The methods comprise applying an adhesive composition between the substrate and the tooth wherein the adhesive composition is formed by the hydrolysis of a bis-acrylate monomer of formula (I) to provide a dicarboxylic acid or a dicarboxylate salt. The present methods are suitable for use in bonding a variety of substrate materials to teeth.

Additional acrylate and/or methacrylate monomers may also be employed in forming the resins and adhesives used in the compositions and methods, respectively, according to the present invention.

These and additional objects and advantages will be more fully understood in view of the following detailed description.

DETAILED DESCRIPTION

The synthetic dental compositions according to the present invention comprise a resin and an inorganic filler. Suitable inorganic fillers may be any of those commonly employed in the art in dental compositions, including, but not limited to, metal, metal oxides, silica, silicacious materials, carbides and the like. Preferred fillers include quartz, alumina and glass. Additionally, organic fillers such as polyethylene and the like may also be employed. The average filler particle size should be in the range of from about 1 to about 100 microns in order that the compositions exhibit a smooth surface in dental applications. The amount of filler included in the compositions will depend on the particular type of filler employed and the specific use in the composition. Preferably, the compositions of the present invention comprise from about 10 to about 90 weight percent of the resin and from about 90 to about 10 weight percent of the filler.

The resin which is included in the synthetic dental compositions is formed by polymerization of at least one bis-acrylate monomer or at least one multifunctional oligomer. The polymers exhibit relatively low shrinkage and reduced residual unsaturation. The low shrinkage allows the formation of stronger and more durable bonds between the dental compositions and various substrates. Generally, the bis-acrylates and multifunctional oligomers employed in the present compositions permit polymerization to high degrees of conversion at or near ambient reaction conditions and can result in resins having relatively high glass transition temperatures.

The bis-acrylate monomers employed in the compositions are of the formula

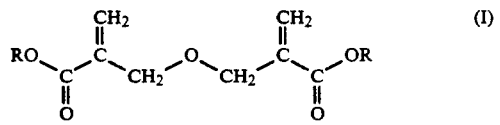

wherein R is selected from the group consisting of alkyl groups having 1 to 6 carbon atoms and aryl substituted alkyl groups in which the alkyl portion has 1 to 6 carbon atoms. Variation of the ester group allows variation in the properties of both the monomer and the resulting polymer resin. As will be demonstrated below, the ester group does not serve as a point of attachment in the resulting polymer. Particularly suitable compositions have been prepared wherein R is selected from the group consisting of methyl, ethyl, isobutyl and phenethyl.

Generally, the symmetrical bis-acrylate monomers of formula (I) are prepared by the reaction of an acrylate monomer and formaldehyde, for example paraformaldehyde, in the presence of a catalytic amount of triethylenediamine (DABCO). The initial reaction product comprises alpha-hydroxymethyl acrylate which, on standing, undergoes a base-mediated condensation in the presence of DABCO to provide the bis-acrylate monomer (I). Generally, the reaction proceeds as follows:

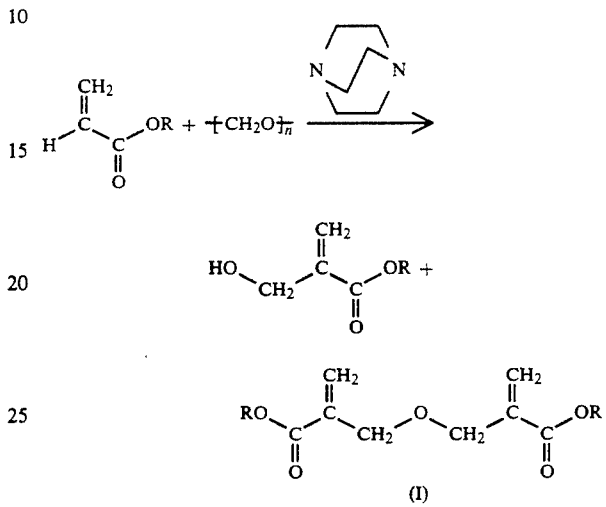

The reaction may be conducted at room temperature or at elevated temperatures up to about 90° C. Preferably, stoichiometric amounts of the acrylate starting material and the paraformaldehyde are employed in order to eliminate the need to remove excess starting materials during product purification. Additionally, the reaction is preferably conducted in a sealed pressure vessel which allows higher temperatures and pressures to be used without material loss. The reaction time may range from approximately 20–40 hours up to several weeks depending on the temperature employed and the specific ester group contained in the acrylate starting material.

The bis-acrylate monomer undergoes homopolymerization and copolymerization in the presence of additional monomers. Owing to the unique spacing of the carbon-carbon double bonds, the bis-acrylate monomers are well suited to undergo an alternating intermolecular-intramolecular cyclopolymerization process. The cyclopolymerization proceeds according to the general reaction:

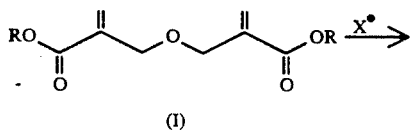

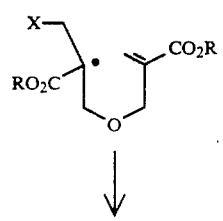

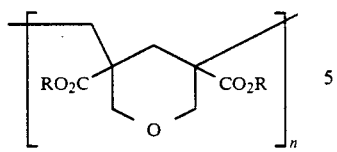

The polymerization may be performed according to bulk polymerization techniques or according to solution polymerization techniques. Generally, the dilute solution polymerization process yields soluble, high molecular weight polymers containing pendant ester functionality and an integral cyclic ether structure and having no significant crosslinked formation. In addition, the solution polymers generally do not display observable residual unsaturation in either IR or NMR spectra. The lack of both crosslinks and unreacted double bonds in the solution polymers indicates that they are exclusively formed by the cyclopolymerization pathway shown above. On the other hand, bulk polymerization generally provides crosslinked polymers, also exhibiting reduced residual unsaturation, for example less than about 10 percent. Both techniques provide good levels of conversion.

Additionally, the bis-acrylate monomers exhibit a significant decrease in the amount of shrinkage which occurs upon polymerization, particularly as compared with polymerization of conventional monomers employed in dental resin applications, for example triethylene glycol dimethacrylate (TEGDMA). One theory to rationalize the dramatically decreased contraction associated with the cyclopolymerization process of the present bis-acrylates involves a preorientation of the carbon-carbon double bonds in the monomer which results in very little shrinkage during the cyclization step. Another possible explanation to account for the diminished shrinkage is that there is simply a larger apparent free volume attributed to a cyclic structure in a polymer compared to that occupied by a rigid linear structure.

The resin which is employed in the synthetic dental compositions of the present invention may alternatively be formed by polymerization of at least one multifunctional oligomer such as that of the formula

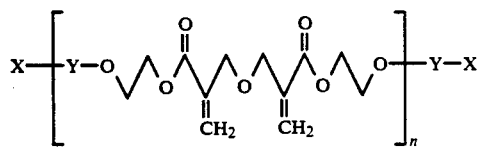

(II)

wherein X is the group

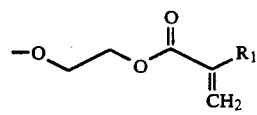

in which $R_1$ is H or $CH_2OH$ and Y is a hydrocarbon group having from about four to about twenty carbon atoms. Preferred Y groups include alkylene groups of from about four to about ten carbon atoms and the group

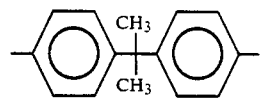

These multifunctional oligomers are capable of several discrete copolymerization reactions per molecule. The high molecular weight, reactive oligomers are prepared by reacting two equivalents of paraformaldehyde with a diacrylate starting material in the presence of a catalytic amount of DABCO. The resulting multifunctional oligomer may be easily precipitated from methanol. The synthesis of the multifunctional oligomer proceeds according to the following general reaction:

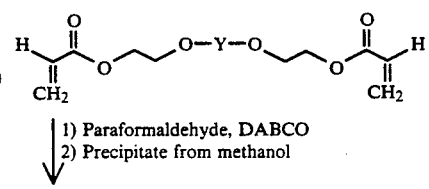

1) Paraformaldehyde, DABCO
2) Precipitate from methanol

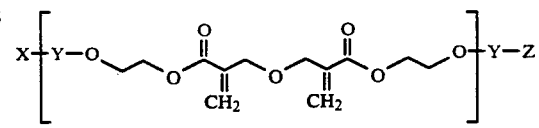

where X and Y are defined as set forth above. Generally, the ratio of the internal bis-acrylate vinyl groups to the terminal hydroxymethyl acrylate vinyl groups gives an average of about 4 repeat units per oligomer molecule. The multifunctional oligomers may similarly be cyclopolymerized to form the resins employed in the present synthetic dental compositions in a manner similar to that discussed above with respect to the bis-acrylate cyclopolymerization. The polymerization of these oligomers yields highly crosslinked polymers which are less brittle in nature than conventional crosslinked diacrylate polymers.

In forming the resins included in the present dental compositions, the at least one bis-acrylate monomer or multifunctional oligomer may be polymerized alone or in combination with additional acrylate and/or methacrylate monomers. Preferably, the bis-acrylate monomer or the multifunctional oligomer comprises at least 10, and more preferably at least 20, weight percent of the monomers which are polymerized to form the resin included in the dental compositions. Preferred comonomers include acrylates and/or methacrylates conventionally employed in dental compositions. Particularly preferred comonomers comprise 2,2-bis[4-(2-hydroxy-3-methacroyloxypropoxy) phenyl] propane (BIS-GMA) and triethylene glycol dimethacrylate (TEGDMA). In forming such copolymers, it has been determined that the ethyl bis-acrylate monomer is well suited to serve as a diluent comonomer in dental resins while the phenethyl bis-acrylate monomer is well suited to serve as a base comonomer in dental resins.

In an alternate embodiment, the invention relates to a method for adhesively bonding a substrate to a tooth. The method comprises applying an adhesive composition between the substrate and the tooth wherein the adhesive composition is formed from a diacid or salt thereof of a hydrolyzed bis-acrylate of formula (I). The diacid is of formula (I) wherein R is H while the diacid salt is of formula (I) wherein R is a metal cation, for example Na+, K+ or the like. The method may be employed for bonding a variety of substrates to a tooth, and may be particularly useful for bonding a synthetic dental composition based on the bis-acrylates of formula (I) to a tooth. The adhesive composition employed in the present methods may be formed from additional comonomers together with the hydrolyzed diacid of the bis-acrylate monomer of formula (I). Preferably, such additional comonomers comprise one or more acrylates or methacrylates, with preferred comonomers comprising BIS-GMA and TEGDMA. The adhesive compositions may also include one or more inorganic fillers in a minor amount as is known in the art. The low shrinkage exhibited by the adhesive compositions formed from the bis-acrylates results in stronger and more durable adhesive bonds.

The compositions of the present invention are illustrated in the following examples.

EXAMPLE 1

This example demonstrates the preparation of a bis-acrylate monomer suitable for use in the compositions and methods of the present invention. A commercially obtained acrylate monomer (70 mmol, used as received) was combined with paraformaldehyde (50 mmol) and a catalytic amount of triethylenediamine (DABCO, 5 mmol) in a stoppered flask. The reaction was allowed to proceed at room temperature with stirring until all (or nearly all) of the paraformaldehyde was consumed as indicated by the transformation of the heterogeneous slurry to a clear solution. After dilution of the reaction mixture with methylene chloride and extraction with dilute aqueous HCl to remove the DABCO, the organic phase was predominantly comprised of the α-hydroxymethyl acrylate intermediate, excess/unreacted starting acrylate and the desired bis-acrylate product. The difunctional monomer was isolated by column chromatography on silica gel with 5-20% ethyl acetate in hexane as eluant. Bis-acrylates of formula (I) in which R was methyl, ethyl, isobutyl and phenethyl, respectively, were prepared according to this procedure. The bis-acrylate monomers were characterized by infrared (Perkin Elmer 1420) and $^1H/^{13}C$ nuclear magnetic resonance (NMR) (JEOL GSX-270) spectroscopy. The reaction time, melting or boiling point and the $^{13}C$ NMR values of the bis-acrylates are set forth in Table I.

TABLE I

| Compound | Monomer Ester, R= | Reaction Time, days | MP (BP), °C. | $^{13}C$ NMR C=O, ppm |
|---|---|---|---|---|
| A | Methyl | 8 | 47 | 166.1 |
| B | Ethyl | 7 | (85/0.1 mm) | 165.7 |
| C | Isobutyl | 22 | (106/0.1 mm) | 165.7 |
| D | Phenethyl | 18 | 43 | 165.6 |

The use of alternative amine catalysts (triethylamine, 4-N-N-dimethyl amino pyridine) and solvents (methylene chloride, tetrahydrofuran) and the replacement of the paraformaldehyde with 1,3,5-trioxane in the above-described procedure all resulted in no observable yield of the bis-acrylate product after a two week reaction period. When a stoichiometric rather than catalytic quantity of DABCO was employed, the formation of the α-hydroxymethyl acrylate intermediate product was greatly enhanced at the expense of the desired bis-acrylate product. The overall yield of the chromatographically purified bis-acrylate monomers varied from about 15 to about 25 percent. The purified bis-acrylates did not appear to elicit the lachramatory response characteristic of the mono-acrylate starting materials and exhibited little or no odor. When stored under refrigeration, the monomers have proven to be stable for months without the addition of any inhibitor.

EXAMPLE 2

This example demonstrates a second procedure for forming the bis-acrylate compounds employed in the present invention. This example is specifically directed to the preparation of the ethyl bis-acrylate. Ethyl acrylate (5.0 g; 50 mmol), paraformaldehyde (1.5 g; 50 mmol) and DABCO (0.56 g; 5 mmmol) were added to a heavy-walled glass ampule. The tube was cooled in a dry ice-acetone bath and then sealed while cold. The reaction was then carried out with the tube submerged in an oil bath at 80° C. The reaction mixture, which was agitated with a small magnetic stir bar, became homogeneous after several hours. After 25 hours, the tube was opened and the slightly cloudy contents were crudely fractionated by chromatography on a silica gel column (5×8 cm) with 20% ethyl acetate in hexane as eluant. Upon evaporation, an 82% yield of the diethyl bis-acrylate was obtained with a purity of greater than 95%. This process is advantageous in that side reaction products are minimized, the reaction time is significantly reduced and the reaction yield is significantly increased as compared with the process described in Example 1.

EXAMPLE 3

This example demonstrates the homopolymerization of bis-acrylate compounds B, C and D from Example 1. Bulk polymerization was conducted in evacuated sealed tubes while dilute solution polymerization was conducted in argon-saturated benzene (2%). An initiator comprising azobis(isobutyronitrile) (0.2 mole %) was employed. Solid state $^{13}C$ NMR using cross-polarization/magic angle spinning techniques was employed to evaluate the degree of cure (conversion) for the cross-linked homopolymers. The results of these measurements are set forth in Table II.

TABLE II

| | | Conversion | |
|---|---|---|---|
| Compound | Monomer Ester, R= | Solution Polymrization, % (60° C.) | Bulk Polymeriation, % (Temp., °C.) |
| B | Ethyl | 100 | 95 (60) |
| | | | 89 (23)* |
| C | Isobutyl | 100 | 93 (60) |
| D | Phenethyl | 100 | 100 (60) |
| | | | 100 (50)** |

*Sample was photopolymerized at ambient temperature.
**Sample was photopolymerized under a sunlamp which maintained the monomer above its melting point.

None of the soluble polymers derived from the solution polymerization displayed any observable residual unsaturation in their IR or NMR spectra. The bulk polymerizations provided only crosslinked polymers. The determination of residual unsaturation was made based on the integrated intensities of the carbonyl resonances arising from the reacted and unreacted acrylate groups at about 177 and 166 ppm, respectively, and was less than about 10%. No attempt was made to extract unreacted monomer from the crosslinked polymers and therefore the residual unsaturation cannot be differentiated between free monomer and constrained, monoreacted units with a pendant unreacted group. The very low levels of residual unsaturation present in this series of polymers indicates that even in bulk polymerizations, the intermolecular cyclopolymerization process operates quite efficiently.

The polymerization shrinkage of the polymers formed from the diethyl bis-acrylate was measured and compared with that of polymers formed from a conventional dimethacrylate employed in dental compositions, namely TEGDMA. The results are set forth in Table III.

TABLE III

| Monomer | MW | Polymerization Temperature, °C. | Conversion, % | Volumetric Shrinkage, % |
|---|---|---|---|---|
| Compound B | 242 | 60 (soln) | 100 | 12.8 |
| | | 60 (bulk) | 95 | 11.6 |
| | | 23 (bulk) | 89 | 11.2 |
| TEGDMA | 286 | 60 (bulk) | 91 | 19.9 |
| | | 37 (bulk)* | 68 | 12.5 |

*Value obtained from Cowperthwaite et al, Polym. Sci. Technol., (1980) 14:208-214.

A comparison of the polymers formed from TEGDMA and the bis-acrylate compound B at similar levels of conversion (approximately 90%) indicates a significant decrease of approximately 40% in the volumetric polymerization contraction for the polymer prepared from the bis-acrylate compound B. When the molecular weights of the monomers are taken into account, the shrinkage exhibited by the polymer of compound B is reduced even further in comparison to that formed of TEGDMA.

EXAMPLE 4

In this example, dental compositions were prepared. The resin included therein was prepared from at least two comonomers, at least one of which comprised a bis-acrylate of formula (I). The filler was a glass filler (Corning 7725, 325 mesh) coated with a 1 weight percent 3-methacryloxypropyl trimethylsilane (Union Carbide A-174). The filler was used in an amount to provide a 4:1 powder-resin ratio. The compositions also included camphorquinone (0.2 weight percent) and ethyl 4-N,N-dimethylamino benzoate (0.7 weight percent) as the photoinitiator system. Specimens were irradiated (40 seconds each side) with a visible light source (L.D. Caulk Prismetics Lite) and subjected to diametral tensile strength (DTS) measurements conducted in compliance with ADA specification 27 for direct filling resins. The monomer formulations used to prepare the compositions together with the measured DTS are set forth in Table IV.

TABLE IV

| Composition | Monomer (wt ratio) | DTS, MPa (sd, n) |
|---|---|---|
| 1 | BIS-GMA/Compound B (75:25) | 52.5 (2.2, 8) |
| 2 | Compound D/TEGDMA (50:50) | 48.3 (4.7, 6) |
| 3 | BIS-GMA/Compound D/ TEGDMA (60:27:13) | 51.7 (2.8, 6) |
| 4 | Compound D/Compound B (70:30) | 29.8 (2.3, 6) |
| 5 | BIS-GMA/TEGDMA (70:30) | 50.5 (1.3, 6) |

With reference to Table IV, Compositions 1-4 are according to the present invention while Composition 5 is a comparative composition In general, there is no significant difference between the comparative composition DTS value and those obtained for compositions according to the present invention. The exception to this is the relatively weak material derived from the resin composed entirely of the bis-acrylate compounds B and D. The decrease in DTS for this composition may be an indication of a low crosslink density brought about by efficient cyclopolymerization. Thus, the use of an effective crosslinking comonomer in conjunction with the bis-acrylate compounds of the present invention in preparing the dental composition resins appears to be advantageous in forming high strength composite materials.

EXAMPLE 5

This example demonstrates preparation of a multifunctional oligomer of formula (II) suitable for use in preparing the dental composition resins of the present invention. An ethoxylated bis-phenol A diacrylate (0.85 g; 1.8 mmol) was combined with paraformaldehyde (0.11 g; 3.6 mmol) and DABCO (0.04 g; 0.4 mmol) in a 1 mL glass ampule. The tube was sealed at atmospheric pressure and then placed in an oil bath at 78° C. for 25 hours. Afterward, the tube was opened and the viscous material was dissolved in 3 ml of methylene chloride. This solution was added dropwise to 60 ml of methanol which resulted in the precipitation of the oligomer. The methanol was decanted and the residual solvent removed under high vacuum to provide the multifunctional oligomer as a viscous, colorless oil in a 74% yield. The $^1H$ NMR analysis indicated no unreacted acrylate end groups. The ratio of the internal bis-acrylate vinyl groups to the terminal hydroxymethyl acrylate vinyl groups provided an average of 4.2 repeat units per oligomer molecule. Polymerization results demonstrated that the resulting oligomer based on the ethoxylated bis-phenol A diacrylate could be homopolymerized to conversions greater than 60%.

EXAMPLE 6

In this example, additional dental compositions were prepared. The resins included therein were prepared from a multifunctional oligomer prepared in accordance with Example 5 and TEGDMA. The weight ratio of the multifunctional oligomer to TEGDMA employed in each composition is set forth in Table V. The dental compositions were prepared in accordance with the general procedure set forth in Example 4 and included a similar glass filler used in an amount to provide a 4:1 powder-resin ratio. The same camphorquinone/ethyl 4-dimethylaminobenzoate photoinitiator system described in Example 4 was also employed in the present dental compositions. The resulting dental compositions were also subjected to DTS measurements as described in Example 4. The results of these measurements are also set forth in Table V.

TABLE V

| Composition | Oligomer/TEGDMA, wt ratio | DTS, MPa (sd, n) |
|---|---|---|
| 6 | 3:1 (max workable viscosity) | 49.4 (1.2, 6) |
| 7 | 2:1 | 51.0 (0.9, 6) |
| 8 | 1:1 (min workable viscosity) | 48.9 (4.4, 5) |

Composition 6 comprising a 3:1 oligomer/TEGDMA weight ratio exhibited the maximum workable viscosity while composition 8 comprising a 1:1 oligomer/TEGDMA weight ratio exhibited the minimum workable viscosity.

The preceding examples are set forth to illustrate specific embodiments of the invention and are not intended to limit the scope of the compositions and methods of the present invention. Additional embodiments and advantages within the scope of the claimed invention will be apparent to one of ordinary skill in the art.

What is claimed is:

1. A synthetic dental composition, comprising
   (a) a resin formed by polymerization of at least one bis-acrylate monomer of the formula $$RO-\underset{\underset{O}{\|}}{C}-\underset{\underset{}{\|}}{\overset{CH_2}{C}}-CH_2-O-CH_2-\underset{\underset{}{\|}}{\overset{CH_2}{C}}-\underset{\underset{O}{\|}}{C}-OR \quad (I)$$

wherein R is selected from the group consisting of alkyl groups having 1 to 6 carbon atoms and aryl substituted alkyl groups in which the alkyl portion has 1 to 6 carbon atoms; and
   (b) an inorganic filler.

2. A synthetic dental composition as defined by claim 1, wherein the resin is formed by polymerization of at least one bis-acrylate monomer of formula I wherein R is selected from the group consisting of methyl, ethyl, isobutyl and phenethyl.

3. A synthetic dental composition as defined by claim 1, wherein the resin is formed by polymerization of said at least one bis-acrylate monomer and at least one additional monomer.

4. A synthetic dental composition as defined by claim 3, wherein said at least one additional monomer is selected from the group consisting of acrylates and methacrylates.

5. A synthetic dental composition as defined by claim 4, wherein said at least one additional monomer is selected from the group consisting of 2,2-bis[4-(2-hydroxy-3-methacroyloxy propoxy) phenyl] propane and triethylene glycol dimethacrylate.

6. A synthetic dental composition as defined by claim 1, wherein the resin is formed by bulk polymerization techniques.

7. A synthetic dental composition as defined by claim 1, comprising from about 10 to about 90 weight percent of the resin and from about 90 to about 10 weight percent of the filler.

8. A synthetic dental composition, comprising
   (a) a resin formed by polymerization of at least one multifunctional oligomer of the formula $$\left[ X-Y-O\diagdown\underset{O}{\overset{O}{\|}}\diagup\diagdown\underset{\underset{CH_2}{\|}}{}\diagup\diagdown\underset{\underset{CH_2}{\|}}{}\diagup\diagdown\underset{O}{\overset{O}{\|}}\diagup O-Y-X \right]_n \quad (II)$$

wherein X is the group $$-O-\overset{O}{\underset{\|}{C}}-\underset{\underset{CH_2}{\|}}{C}-R_1$$

with being selected from the group consisting of H and $CH_2OH$, and Y is a hydrocarbon group having from about four to about twenty carbon atoms; and
   (b) an inorganic filler.

9. A synthetic dental composition as defined by claim 8, wherein Y is a group selected from alkylene groups of from about 4 to about 10 carbon atoms and the group $$-\underset{}{\phantom{x}}\bigcirc\underset{\underset{CH_3}{|}}{\overset{\overset{CH_3}{|}}{C}}\bigcirc\underset{}{\phantom{x}}-.$$

10. A synthetic dental composition as defined by claim 8, wherein the resin is formed by polymerization of said at least one multifunctional oligomer and at least one additional monomer.

11. A synthetic dental composition as defined by claim 9, wherein said at least one additional monomer is selected from the group consisting of acrylates and methacrylates.

12. A synthetic dental composition as defined by claim 11, wherein said at least one additional monomer is triethylene glycol dimethacrylate.

13. A synthetic dental composition as defined by claim 8, comprising from about 10 to about 90 weight percent of the resin and from about 90 to about 10 weight percent of the filler.

14. A method for adhesively bonding a substrate to a tooth, comprising applying an adhesive composition between the substrate and the tooth, said adhesive composition being formed by the hydrolysis of a bis-acrylate monomer yielding a dicarboxylic acid or a dicarboxylate salt of the formula $$RO-\underset{\underset{O}{\|}}{C}-\underset{\underset{}{\|}}{\overset{CH_2}{C}}-CH_2-O-CH_2-\underset{\underset{}{\|}}{\overset{CH_2}{C}}-\underset{\underset{O}{\|}}{C}-OR \quad (I)$$

wherein R is H or a metal cation.

15. A method as defined by claim 14, wherein said adhesive composition further is formed from at least one additional monomer.

16. A synthetic dental composition as defined by claim 15, wherein said at least one additional monomer is selected from the group consisting of acrylates and methacrylates.

17. A synthetic dental composition as defined by claim 16, wherein said at least one additional monomer is selected from the group consisting of 2,2-bis[4-(2-hydroxy-3-methacroyloxy propoxy) phenyl] propane and triethylene glycol dimethacrylate.

18. A method as defined by claim 14, wherein said adhesive composition further comprises an inorganic filler.

* * * * *